(12) United States Patent
Rubben (10) Patent No.: US 9,569,586 B2
(45) Date of Patent: Feb. 14, 2017

(54) ALGORITHM FOR MODIFICATION OF SOMATIC CANCER EVOLUTION

(76) Inventor: Albert Rubben, Aachen (DE)

( * ) Notice: Subject to any disclaimer, the term of this patent is extended or adjusted under 35 U.S.C. 154(b) by 191 days.

(21) Appl. No.: 14/374,924

(22) PCT Filed: Feb. 13, 2012

(86) PCT No.: PCT/EP2012/052437
§ 371 (c)(1),
(2), (4) Date: Jul. 28, 2014

(87) PCT Pub. No.: WO2013/120509
PCT Pub. Date: Aug. 22, 2013

(65) Prior Publication Data
US 2015/0072865 A1    Mar. 12, 2015

(51) Int. Cl.
*G01N 33/48*    (2006.01)
*G01N 33/50*    (2006.01)
(Continued)

(52) U.S. Cl.
CPC .............. *G06F 19/18* (2013.01); *G01N 33/574* (2013.01); *G06F 19/14* (2013.01); *G06F 19/24* (2013.01); *G06F 19/3431* (2013.01); *G06F 19/12* (2013.01)

(58) Field of Classification Search
None
See application file for complete search history.

(56) References Cited

FOREIGN PATENT DOCUMENTS

EP    2189919 A1 * 11/2008

OTHER PUBLICATIONS

Navin et al. Tumour evolution inferred by single-cell sequencing. Nature, vol. 472, 2011, pp. 90-94.*

\* cited by examiner

*Primary Examiner* — Russell S Negin
(74) *Attorney, Agent, or Firm* — Mark M. Friedman (57) ABSTRACT

Most clinically distinguishable malignant tumors are characterized by specific mutations, specific patterns of chromosomal rearrangements and a predominant mechanism of genetic instability. It has been suggested that the internal dynamics of genomic modifications as opposed to the external evolutionary forces have a significant and complex impact on Darwinian species evolution. A similar situation can be expected for somatic cancer evolution as the key mechanisms encountered in species evolution such as duplications, rearrangements or deletions of genes also constitute prevalent mutation mechanisms in cancers with chromosomal instability. The invention is an algorithm which is based on a systems concept describing the putative constraints of the cancer genome architecture on somatic cancer evolution. The algorithm allows the identification of therapeutic target genes in individual cancer patients which do not represent oncogenes or tumor suppressor genes but have become putative therapeutic targets due to constraints of the cancer genome architecture on individual somatic cancer evolution. Target genes or regulatory elements may be identified by their designation as essential genes or regulatory elements in cancer cells of the patient but not in normal tissue cells or they may be identified by their impact on the process of somatic cancer evolution in individual patients based on phylogenetic trees of somatic cancer evolution and on the constructed multilayered cancer genome maps. The algorithm can be used for delivering personalized cancer therapy as well as for the industrial identification of novel anti-cancer drugs. The algorithm is essential for designing software programs which allow the prediction of the natural history of cancer disease in individual patients.

9 Claims, 3 Drawing Sheets

(51) Int. Cl.
*G06F 19/18* (2011.01)
*G06F 19/14* (2011.01)
*G06F 19/24* (2011.01)
*G01N 33/574* (2006.01)
*G06F 19/00* (2011.01)
*G06F 19/12* (2011.01)

ALGORITHM FOR MODIFICATION OF SOMATIC CANCER EVOLUTION

BACKGROUND

Field of Invention

The invention relates to the field of targeted cancer therapy. In particular, the invention relates to the identification of therapeutic target genes in individual cancer patients which do not represent oncogenes or tumor suppressor genes but have become putative therapeutic targets due to constraints of the cancer genome architecture on individual somatic cancer evolution.

Background Art

Cancer as a devastating but variable disease has always been subject of various theories, many of them sharing an explicit or implicit holistic or systems approach. Today, the scientific community has widely accepted the concept that cancer is caused by changes within the cellular genome [Knudson 1971, Fearon and Vogelstein, 1990]. This view may be regarded as a specification of Boveri's idea that somatic mutations are the basis of cancer [Boveri 1914].

Tumorigenesis and tumor progression can be considered an evolutionary process in which mutant and more tumorigenic subpopulations are sequentially selected and derived from less tumorigenic or benign progenitor cells [Foulds 1954, Nowell 1976, Gatenby and Vincent 2003]. The two main driving forces of tumorigenesis are on one hand a positive growth selection which may be mediated by external influences as well as by mutations in genes responsible for cell growth and apoptosis regulation and on the other hand an enhanced mutation rate leading to genetic instability.

Several human diseases are associated with an enhanced mutation rate and a predisposition to cancer. The mechanisms leading to genomic instability are multiple as multiple different systems exist which maintain genome integrity and which target different forms of DNA damage. The best known examples of genomic instability are post replicative mismatch repair (MMR) deficiency leading to mutations of short repetitive sequences such as microsatellite DNA (microsatellite instability=MIN) and chromosomal instability (=CIN) which induces rearrangement, loss, amplification or duplication of chromosomes or chromosome fragments resulting in aneuploidy. Besides, various other mechanisms exist such as defective nucleotide excision repair (NER), defective base excision repair (BER) and defective cell cycle checkpoint controls. It has been shown that human tumors with deficiency of MMR display different mutation patterns at target genes involved in carcinogenesis than tumors with chromosomal instability (CIN) [Zhou et al. 2002]. DNA-repair systems such as MMR and NER are constituted of multiple proteins and defects of different factors within a DNA repair system may result in differing mutation frequencies, mutation spectra and mutation hotspots within coding and non-coding DNA. This has been demonstrated in bacterial, yeast and animal models [Schaaper and Dunn et al. 1987, Habraken et al. 1996, Marti et al. 2003, Harfe and Jinks-Robertson 2000, Denver et al. 2006, Denver et al. 2005, Yao et al. 1999, Kuraguchi et al. 2001, Andrew et al. 2000]. Defects of mechanisms ensuring chromosomal stability such as lack of repair of double strand breaks, telomere loss, centrosome amplification, homologous recombination deficiency or suppression of hyperrecombination do also induce specific types of mutations [Lobachev et al. 2002, Traverso et al. 2003, Sabatier of al. 2005; Michor 2005, Deans et al. 2003; Saunders 2005, Bailey and Murnane 2006].

Most clinically distinguishable malignant tumors are characterized by specific mutations, specific patterns of chromosomal rearrangements and a predominant mechanism of genetic instability but it remains unsolved whether modifications of cancer genomes can be explained solely by mutations and positive or negative selection through the cancer microenvironment It has been suggested that the internal dynamics of genomic modifications as opposed to the external evolutionary forces have a significant and complex impact on Darwinian species evolution [Conrad 1990, Shapiro 1999, Dover 2000, Poole et al. 2003, Brookfield 2009]. A similar situation can be expected for somatic cancer evolution as the key mechanisms encountered in species evolution such as duplications, rearrangements or deletions of genes [Demuth et a 2006] also constitute prevalent mutation mechanisms in cancers with chromosomal instability.

DISCLOSURE OF THE INVENTION

Technical Problem

Recognition of Constraints of the Genome Architecture on Somatic Cancer Evolution

BASIC ASSUMPTIONS AND DEFINITIONS

Figure 1:
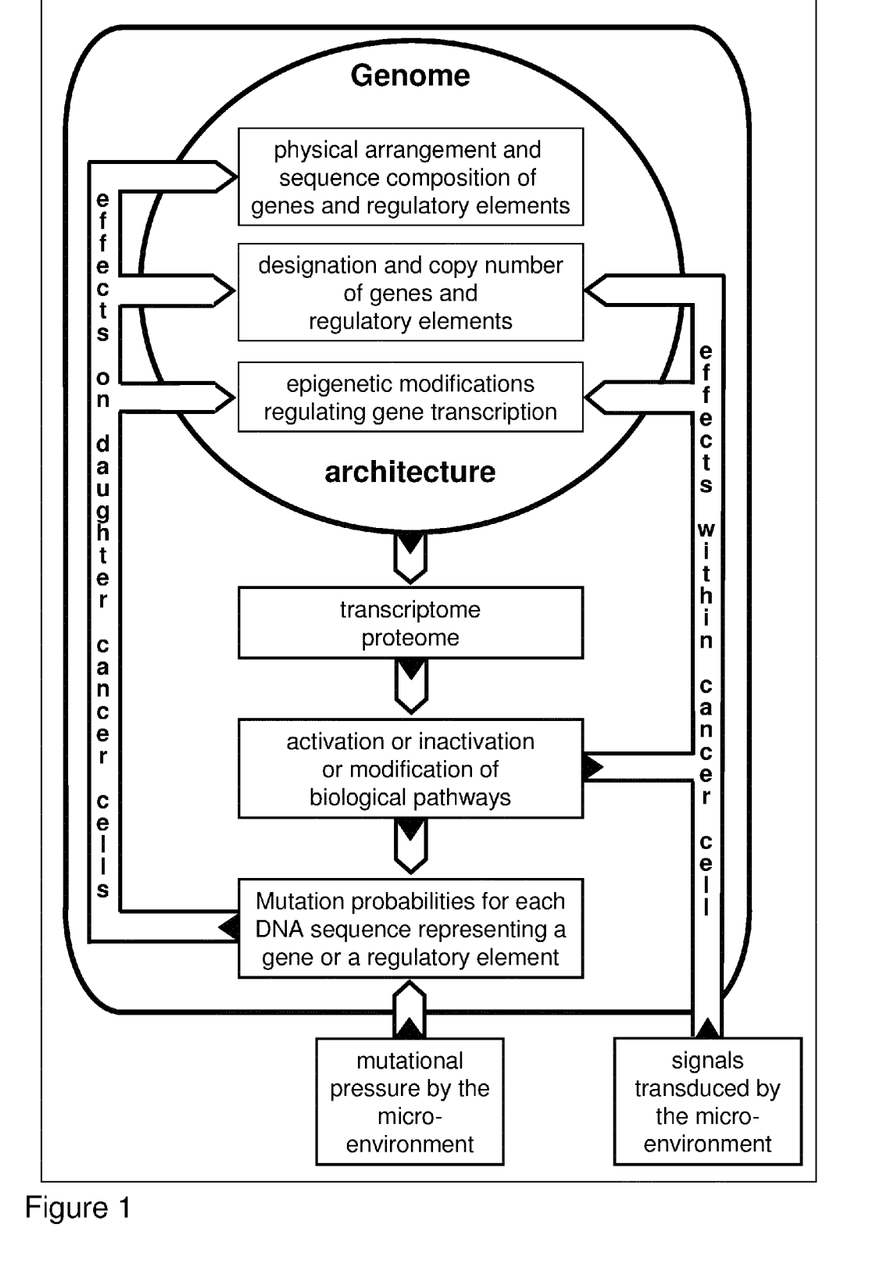
FIG. 1: Interdependency of cancer genome architecture and somatic cancer evolution.

1) The principal hypothesis leading to the described invention is that permissive or restrictive effects of the genome architecture on lineage selection during somatic cancer evolution exist and have an impact which is comparable in magnitude to the effects of selection by the tumor microenvironment (FIG. 1). This hypothesis is the basis of a systems approach which defines constraints of the genome architecture on lineage selection and evolvability during somatic cancer evolution. Dissection of putative mechanisms mediating constraints exerted by the genome architecture on somatic cancer evolution provide an algorithm for understanding and predicting as well as modifying somatic cancer evolution in individual patients.

2) The term 'genome architecture' stands for the cell genome as a whole and has been chosen to underline that its influence on somatic cancer evolution is not only determined by the coding and regulatory sequences but also by the physical arrangement of the coding and regulatory sequences within chromosomes or chromosome fragments as well as by chromatin organization and nuclear topology of chromosomes. It relates to the term 'genome system architecture', used by Shapiro in order to describe species evolution as a systems engineering process [Shapiro 1999].

3) The genome architecture comprises five structural aspects:

(i) base composition of genes, of regulatory elements and of foreign (viral) DNA/RNA sequences, (ii) presence and copy number of wild type or mutated genes, of regulatory elements, and of foreign (viral) DNA/RNA sequences, (iii) physical arrangement of genes of regulatory elements, and of foreign (viral) DNA/RNA sequences within chromosomes, including rearrangements of chromosomes or chromosome fragments, as well as within mitochondrial DNA, (iv) chromatin organization including epigenetic modifications, interaction of DNA with RNAs and nuclear proteins and nuclear topology of chromosomes, (v) status of gene transcription. Chromatin organization, epigenetic modifications and transcriptional status are interrelated but are considered independently as not all changes of chromatin organization or epigenetic modifications are reflected by changes in gene transcription.

4) Somatic cancer evolution describes the occurrence of preneoplastic cells and of derived cancer cells of monoclonal origin in an individual organism as well as the further development of derived cancer cell populations and cancer subclones during the processes of cancer progression.

5) Genomic instability in cancer is the result of mutations of specific genes in most cases.

6) Various types of genomic instability promote different and specific mutations of individual genes, of regulatory elements, of non-coding DNA, of chromosomes and chromosome fragments depending on the base composition, sequence context, physical arrangement of the target DNA sequences in the genome and depending on the transcriptional status of the cell. As mutation acquisition itself is a stochastic process, specificity in this context means that the type of genomic instability affects mutation probabilities in cancer daughter cells and that these mutations probabilities may be determined a priori.

7) Lineage selection in Darwinian species evolution describes an evolutionary process which favours long-term fitness whenever there is a conflict between the short- and the long-term effects of selection [Nunney 1989, Nunney 1999]. It is assumed that lineage selection is present as well in cancer cell subclones which arise during the process of somatic cancer evolution. A change of the genome architecture of a cell of cancer lineage may have immediate effects within one cancer evolution stage or may induce long-term effects on lineage selection. The immediate effects of the modified genome architecture on cancer evolution manifest themselves prior to the acquisition of additional mutations. The destiny of the new tumor cell subclone will be determined by changes in tumor cell fitness within the original or a new anatomical compartment. Provided that no extinction of the subclone occurs prior to acquisition of additional mutations, the initial mutation will also affect further evolution of daughter cell lineages within the original microenvironment or at later stages of clinical tumor progression. These later effects of the initial mutation are the effects on lineage selection.

Constraints of the Genome Architecture on Lineage Selection During Somatic Cancer Evolution:

Three classes of lineage selection effects can be distinguished:

1) Lineage selection effects mediated by cancer cell fitness:

Changes of the genome architecture may enhance or decrease fitness of cancer cell lineages during later stages of tumor cell evolution.

2) Lineage selection effects mediated by changes of mutation probability:

The second class of lineage selection effects is mediated by changes of mutation probabilities of individual genes, regulatory elements, chromosomes and chromosome fragments. Mutations resulting in genomic instability induce lineage selection effects as stochastic mutations which arise in genetically unstable cells of cancer lineage are non-random with regards to mutation probability and mutation patterns. Mutations which induce genomic instability have a strong influence on further evolution of a tumor cell lineage as they will increase or decrease the probability that a specific fitness enhancing or fitness decreasing mutation will occur at later stages of tumor cell evolution. The fact, that genetic instability is a hallmark of most human cancers [Beckman and Loeb 2005] and is often already detected in preneoplastic lesions [Tsao et al. 1999, Cohn et al. 2001], by itself demonstrates that cells of cancer lineage harbouring mutations leading to genetic instability tend to be positively selected during the process of tumor cell evolution.

3) Lineage selection effects mediated by changes of gene designation and of physical and functional genome redundancy:

The third class of lineage selection effects results of changes of functional gene designation and physical and functional genome redundancy.

A physical DNA stretch in a cell of cancer lineage representing a gene or a regulatory element may have various biological functions. With focus on somatic cancer cell evolution, one may divide the functions in two basic categories with few specific attributes:

First, functions with regards to cell survival within a specific clinical stage and microenvironment of a cell of cancer lineage and second, the functions with regards to transition of a cell of cancer lineage to a new clinical stage or microenvironment. For each biological function of a gene or regulatory element, attributes of both categories may be combined.

Within a clinical stage or microenvironment, functions of wild type or mutated genes or regulatory elements may be essential to sustain cell survival. Genes or regulatory elements with one or more essential functions are designated essential genes within the proposed mechanistic systems approach. Genes or regulatory elements displaying functions which modify the fitness of a cell of cancer lineage in a given clinical stage or microenvironment may be considered non essential fitness modifying genes while genes with functions without any apparent consequence on cellular fitness will be considered fitness neutral genes.

With regards to the role in the evolutionary process, functions of wild type or mutated genes or regulatory elements may inhibit, promote or accelerate the evolutionary process. Genes which inhibit tumor cell evolution, are considered tumor suppressor genes or gatekeeper genes [Sidransky 1996, Kinzler and Vogelstein 1997] while genes which promote carcinogenesis or tumor progression when they are amplified, activated or have acquired a gain of function mutation are oncogenes. Genes or regulatory elements which are implicated in the maintenance of the genomic integrity are called caretaker genes. Mutations of caretaker genes but also changes of expression levels of caretaker genes may lead to genomic instability and thus accelerate tumor cell evolution [Kinzler and Vogelstein 1997].

The designation of a gene or regulatory element within this scheme, i.e. an essential gene, a non essential fitness modifying gene, a fitness neutral gene, a tumor suppressor/gatekeeper gene, an oncogene or a caretaker gene is fundamental for lineage selection effects through changes in physical or functional genome redundancy.

Physical genome redundancy is the copy number of identical genetic sequences. Functional genome redundancy of a gene or a regulatory element is defined as the number of different genetic elements, regardless of copy number, coding for the same specific biological function within a cancer genome architecture. Functional genome redundancy is lost when only one specific DNA sequence, regardless of its copy number, assumes a specific biological function within a cancer cell at a specific progression state during the process of somatic cancer cell evolution. Functional genome redundancy of a gene or a regulatory element acts together with copy number changes in order to affect lineage selection effects.

A mutation within a cell of cancer lineage may reduce or amplify the copy number of a specific gene or regulatory element without a direct effect on tumor cell fitness in the original anatomical compartment or progression stage. The resulting increase or decrease of the copy number may, nevertheless, determine the functional effect of a secondary mutation which arises later during tumor evolution and which targets an additional copy of the gene or regulatory element when the gene or regulatory element has no functional redundancy or when functional redundancy has been lost through additional mutations.

Figure 2:
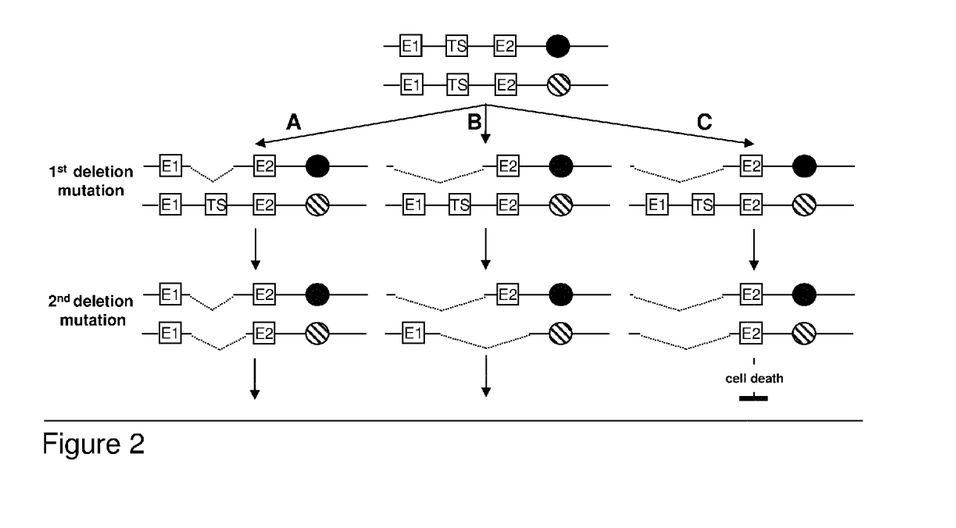
FIG. 2: Schematic drawing of effects of nearby essential genes on position and size of deletion mutations. E1 and E2 indicate essential genes while TS indicates a tumor suppressor gene on a chromosome. A, B and C show three possible mutation sequences leading to homozygeous loss of one tumor suppressor on homologue chromosomes. Paths A and B result in viable cells while path C results in cell death.

The two-hit process postulated by Knudson [Knudson 1971] falls within this class of lineage selection effects. The first inactivating mutation reduces a tumor suppressor gene to hemizygosity such as the retinoblastoma gene but has no direct phenotypic effect. Only the second mutation deletes tumor suppressor function and promotes tumor cell evolution. A more complex situation arises, when a large DNA deletion reduces physical genome redundancy of multiple genes. For example, one copy of a tumor suppressor gene could be codeleted with one copy of a neighboring essential gene. Reduction of copy number of the essential gene would display a restricting effect on subsequent tumor cell evolution as it restricts transition to a progression state with complete loss of tumor suppressor function to mutations which do not delete the remaining copy of the essential gene (FIG. 2). Duplications or further amplifications of chromosomes or chromosome fragments may have an immediate effect on fitness of cells of cancer lineage by enhancing the copy number of oncogenes. On the other hand, co-amplified sequences may contain genes which may act as tumor suppressor genes at later stages of tumor progression. Therefore, amplifications of genetic material may also display lineage selection effects.

Functional genome redundancy may be altered by changes in the designation of genes and regulatory elements. For example, a mutation which constitutively activates a protein within a signal transduction pathway consisting of multiple proteins and which is essential for cell survival would not only shorten the regulatory pathway but would also create an essential gene which is only present as a single sequence. It would further change the designation of genes with functions upstream in the signal transduction pathway from essential to non essential fitness modifying or fitness neutral genes. These genes may then be more readily deleted hemizygously or homozygously in genetically unstable cells of cancer lineage resulting in further reduction of functional genome redundancy. There are data suggesting that a reduction of redundancy in cancer cells might be found at cdk genes where aberrant expressions and amplifications are frequently detected [Berthet & Kaldis 2007, Schmidt et al. 1994]. Besides shortening of signal transduction pathways, mutations may also induce re-wiring of signal transduction pathways [Pawson & Warner 2007] and remodelling of key biologic processes including alterations of the protein-protein, protein-DNA and RNA-DNA interactome with similar putative effects on multiple pathways and processes.

Tertiary Therapeutic Target Genes Resulting from Constraints of the Tumor Cell Architecture on Somatic Tumor Cell Evolution:

If the clinical course of cancer is considered a dynamic process regulated by biological needs and stochastic events which can be described mathematically, then knowledge of constraints of the tumor cell architecture on lineage selection during somatic tumor cell evolution can be used to modify tumor cell evolution as well as the clinical course of the malignant disease in individual cancer patients.

Activated oncogenes which initiate malignant transformation of a specific malignancy may be considered primary therapeutic target genes in oncology. Highly efficient medicaments have already been developed which target cancer driving oncogene mutations in a number of defined human malignancies [Verweij et al. 2008]. Fully inactivated tumor suppressor genes may be regarded as secondary therapeutic targets. Although abrogated tumor suppressor pathways represent stable cancer signatures in case of mutations of both tumor suppressor alleles, they are more difficult to exploit for pharmacological or genetic therapies. Most current research focuses on the p53 pathway and demonstrates first promising results [Wiman 2006].

The proposed systems approach postulates a third group of target genes which do not belong to oncogenes or tumor suppressor genes but have become putative therapeutic targets due to constraints of the tumor cell architecture on somatic cancer cell evolution in individual patients.

Problems Related to the Identification of Lineage Effects of the Cancer Genome Architecture on Somatic Cancer Evolution:

Large amount of data on the human genome as well as on various human cancer genomes have been obtained in recent years by genome-wide sequencing, genome-wide expression analysis [DeRisi et al. 1996, Schena 1996], proteome analysis, genome-wide copy number analysis as well as by combinations of these methods [Green et al. 2011]. Computational approaches such as cluster analysis [Eisen et al. 1998] or self-organizing maps [Tamayo et al. 1996] have been applied in order to extract biological information out of extensive data points generated by these techniques. Patterns detected in gene expression or in copy number changes of specific cancers suggest that cancer genomes emerge and evolve through a multitude of different but still finite evolutionary pathways. One may expect that the restrictive effects of the genome architecture on lineage selection during somatic cancer evolution will be contained in these data sets as well as in patterns and clusters generated by supervised or unsupervised data mining algorithms using the available data.

Nevertheless, comparing genome-scale mutation data as well as transcriptome and proteome data of multiple cancers of the same entity might not be sufficient to identify target genes for anticancer therapy which do not belong to oncogenes or tumor suppressor genes but have become putative therapeutic targets due to constraints of the cancer cell genome architecture on somatic tumor evolution in individual patients. Several reasons may account for the limitations of an approach which extracts patterns out of genome wide analysis of multiple cancers of one entity: Pattern analysis will be more likely to detect genes which are overexpressed or homozygeously deleted, i.e. the classical oncogenes or tumor suppressor genes, than genes, which show only low or temporarily restricted expression in a cancer or which are hemizygeously deleted but nevertheless represent essential genes for survival of the cancer. The magnitude of expression of a gene as well as the differential expression of a gene in cancer tissue does not per se indicate whether the gene and its expression are essential for survival of cancer cells. In addition, even if progression of cancer genomes might follow only a finite number of evolutionary pathways, it can be expected that many genes might become putative therapeutic targets only in few patients due to the random nature of the mutation process and the multitude of involved genes. Furthermore, it has to be taken into account, that genome-scale gene expression and gene copy number data are not obtained from single genomes but from cancer cell populations which are highly heterogeneous due to underlying genetic instability. Therefore, predominating gene expression patterns or copy number changes detected in cancer tissue of a specific progression stage might not be representative of the cancer cells which have the ability to progress to more advanced tumor stages and which should be targeted by therapy.

REFERENCES

Andrew S E, Xu X S, Baross-Francis A, Narayanan L, Milhausen K et al. (2000) Mutagenesis in PMS2- and MSH2-deficient mice indicates differential protection from transversions and frameshifts. Carcinogenesis 21: 1291-1295.

Bailey S M, Murnane J P (2006) Telomeres, chromosome instability and cancer Nucleic Acids Res 34: 2408-2417.

Beckman R A, Loeb L A (2005) Genetic instability in cancer: theory and experiment. Semin Cancer Biol 15: 423-435.

Berthet C, Kaldis P (2007) Cell-specific responses to loss of cyclin-dependent kinases. Oncogene 26: 4469-4477.

Boveri T (1914) Zu Frage der Entstehung maligner Tumoren, Gutav Fischer Verlag, Jena, Germany.

Brookfield J F (2009) Evolution and evolvability: celebrating Darwin 200. Biol Lett 5: 44-46.

Cohn D E, Mutch D G, Herzog T J, Rader J S, Dintzis S M et al. (2001) Genotypic and phenotypic progression in endometrial tumorigenesis: Determining when defects in DNA mismatch repair and KRAS2 occur. Genes Chromosomes Cancer 32: 295-301.

Conrad M (1990) The geometry of evolution. Biosystems 4: 61-81.

Deans B, Griffin C S, O'Regan P, Jasin M, Thacker J (2003) Homologous recombination deficiency leads to profound genetic instability in cells derived from Xrcc2-knockout mice. Cancer Res 63: 8181-8187.

Demuth J P, Bie T D, Stajich J E, Cristianini N, Hahn M W (2006) The evolution of Mammalian gene families. PLoS ONE 20; 1:e85.

Denver D R, Feinberg S, Estes S, Thomas W K, Lynch M (2005) Mutation rates, spectra and hotspots in mismatch repair-deficient Caenorhabditis elegans. Genetics 170: 107-113.

Denver D R, Feinberg S, Steding C, Durbin M, Lynch M (2006) The relative roles of three DNA repair pathways in preventing Caenorhabditis elegans mutation accumulation. Genetics 174: 57-65.

DeRisi J, Penland L, Brown P O, Bittner M L, Meltzer P S et al. (1996) Use of a cDNA microarray to analyse gene expression patterns in human cancer. Nat Genet 14: 457-460.

Dover G (2000) How genomic and developmental dynamics affect evolutionary processes. Bioessays 22: 1153-1159.

Eisen M B, Spellman P T, Brown P O, Botstein D (1998) Cluster analysis and display of genome-wide expression patterns. Proc Natl Acad Sci USA 95: 14863-14868.

Fearon E R, Vogelstein B (1990) A genetic model for colorectal tumorigenesis. Cell 61: 759-67.

Foulds (1954) The experimental study of tumor progression: A review. Cancer Res 14: 327-339.

Gatenby R A, Vincent T L (2003) An evolutionary model of carcinogenesis. Cancer Res 63: 6212-6220.

Green M R, Aya-Bonilla C, Gandhi M K, Lea R A, Wellwood J et al. (2011) Integrative genomic profiling reveals conserved genetic mechanisms for tumorigenesis in common entities of non-Hodgkin's lymphoma. Genes Chromosomes Cancer 50: 313-326.

Habraken Y, Sung P, Prakash L, Prakash S (1996) Binding of insertion/deletion DNA mismatches by the heterodimer of yeast mismatch repair proteins MSH2 and MSH3. Curr Biol 6: 1185-1187.

Harfe B D, Jinks-Robertson S (2000) Sequence composition and context effects on the generation and repair of frameshift intermediates in mononucleotide runs in Saccharomyces cerevisiae. Genetics 156: 571-578.

Kinzler K W, Vogeistein B (1997) Cancer-susceptibility genes. Gatekeepers and caretakers. Nature 386: 761, 763.

Knudson A G (1971) Mutation and cancer: statistical study of retinoblastoma. Proc Natl Acad Sci USA 68: 820-823.

Kuraguchi M, Yang K, Wong E, Avdievich E, Fan K et al. (2001) The distinct spectra of tumor-associated Apc mutations in mismatch repair-deficient Apc1638N mice define the roles of MSH3 and MSH6 in DNA repair and intestinal tumorigenesis. Cancer Res 61: 7934-7942.

Lobachev K S, Gordenin D A, Resnick M A (2002) The Mre11 complex is required for repair of hairpin-capped double-strand breaks and prevention of chromosome rearrangements. Cell 108: 183-193.

Marti T M, Mansour A A, Lehmann E, Fleck O (2003) Different frameshift mutation spectra in non-repetitive DNA of MutSalpha- and MutLalpha-deficient fission yeast cells. DNA Repair (Amst) 2: 571-580.

Michor F (2005) Chromosomal instability and human cancer. Philos Trans R Soc Lond B Blot Sci 360: 631-635.

Nowell P C (1976) The clonal evolution of tumor cell populations. Science 194: 23-28.

Nunney L (1989). The maintenance of sex by group selection. Evolution 43: 245-257.

Nunney L (1999) Lineage selection and the evolution of multistage carcinogenesis. Proc Biol Sci 266: 493-498.

Pawson T, Warner N (2007) Oncogenic re-wiring of cellular signaling pathways. Oncogene 26: 1268-1275.

Poole A M, Phillips M J, Penny D (2003) Prokaryote and eukaryote evolvability. Biosystems 69: 163-185.

Sabatier L, Ricoul M, Pottier G, Murnane J P (2005) The loss of a single telomere can result in instability of multiple chromosomes in a human tumor cell line. Mol Cancer Res 3: 139-150.

Saunders W (2005) Centrosomal amplification and spindle multipolarity in cancer cells. Semin Cancer Biol 15: 25-32.

Schaaper R M, Dunn R L (1987) Spectra of spontaneous mutations in *Escherichia coil* strains defective in mismatch correction: the nature of in vivo DNA replication errors. Proc Natl Acad Sci USA 84: 6220-6224.

Schena M (1996) Genome analysis with gene expression microarrays. Bioessays 18: 427-431.

Schmidt E E, Ichimura K, Reifenberger G, Collins V P (1994) CDKN2 (p16/MTS1) gene deletion or CDK4 amplification occurs in the majority of glioblastomas. Cancer Res 54: 6321-6324.

Shapiro J A (1999) Genome system architecture and natural genetic engineering in evolution. Ann N Y Acad Sci 870: 23-35.

Sidransky D (1996) Is human patched the gatekeeper of common skin cancers? Nat Genet 14: 7-8.

Tamayo P, Slonim D, Mesirov J, Zhu Q, Kitareewan S et al. (1999) Interpreting patterns of gene expression with self-organizing maps: methods and application to hematopoietic differentiation. Proc Natl Acad Sci USA 96: 2907-2912.

Traverso G, Bettegowda C, Kraus J, Speicher M R, Kinzler K W et al. (2003) Hyper-recombination and genetic instability in BLM-deficient epithelial cells. Cancer Res 63: 8578-8581.

Tsao J L, Tavare S, Salovaara R, Jass J R, Aaltonen L A et al. (1999) Colorectal adenoma and cancer divergence. Evidence of multilineage progression. Am J Pathol 154: 1815-1824.

Verweij J, Seynaeve C, Sleijfer S (2008) GIST as the model of paradigm shift towards targeted therapy of solid tumors: update and perspective on trial design. Adv Exp Med Biol 610: 144-154.

Wiman K G (2006) Strategies for therapeutic targeting of the p53 pathway in cancer. Cell Death Differ 13: 921-926.

Yao X, Buermeyer A B, Narayanan L, Tran D, Baker S M et al. (1999) Different mutator phenotypes in versus Pms2-deficient mice. Proc Natl Acad Sci USA 96: 6850-6855.

Zhou X P, Loukola A, Salovaara R, Nystrom-Lahti M, Peltomaki P et al. (2002) PTEN mutational spectra, expression levels, and subcellular localization in microsatellite stable and unstable colorectal cancers. Am J Pathol 161: 439-447.

Solution to Problem

Figure 3:
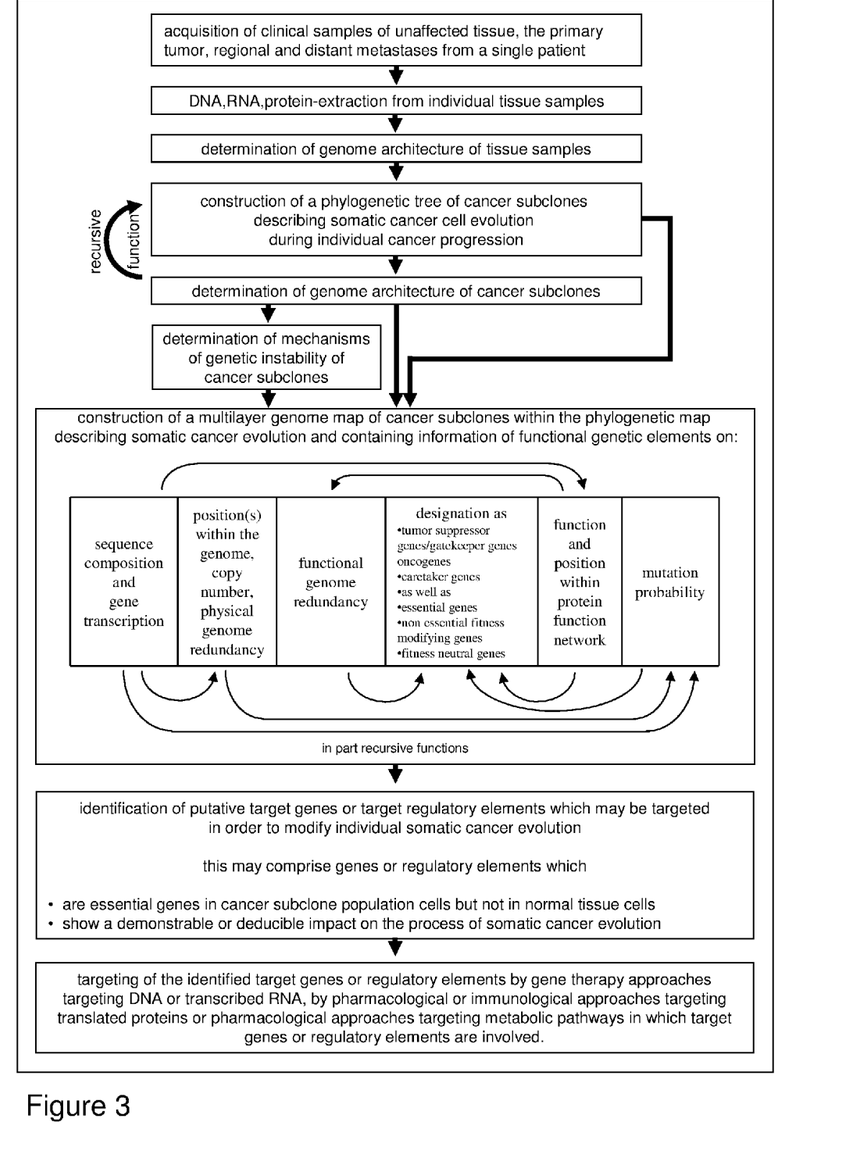
FIG. 3: Algorithm for modifying cancer progression in human cancers based on lineage effects of the cancer genome architecture on somatic cancer evolution.

Algorithm for Modifying Cancer Progression in Human Cancers Based on Lineage Effects of the Cancer Genome Architecture on Somatic Cancer Evolution In order to overcome the above described limitations but still use the wealth of information generated by genome-scale molecular analysis techniques, an integrative approach is proposed to search for putative tertiary therapeutic targets in human cancers (FIG. 3). It primarily focuses on the comparison of genome-wide molecular data obtained from cancer material of the same patient but of different progression stages as the constraints of the cancer genome architecture on somatic cancer evolution can best be detected when considering the phylogenetic tree of cancer subclones. In addition, construction of a phylogenetic tree of cancer subclones and their evolution allows eliminating confounding data points generated by genetic instability and by admixture of cancer subclones which represent evolutionary dead ends.

The Proposed Algorithm for Modifying Somatic Cancer Progression Consists of the Following Steps:

1. Acquisition of tumor material of a human cancer with multiple samples of an individual patient representing unaffected tissue, primary tumor as well as regional and distant metastases.

2. Construction of a map of clinical cancer progression in the patient based on the anatomical and temporal occurrence of the primary tumor and its metastases.

3. Extraction of DNA, RNA and proteins of unaffected tissue and of samples of the primary tumor as well as of regional and distant metastases from the patient representing clinical cancer progression.

4. Determination of the cancer genome architecture of the analyzed tissue samples by determination of RNA and protein expression, of karyotypes, of gene losses and gains as well as of gene allele losses in tumor tissues.

5. Construction of a preliminary phylogenetic tree of somatic cancer evolution based on steps 2 to 4 by supervised or unsupervised clustering of the genetic data obtained by step 4.

6. Construction of a phylogenetic tree of somatic cancer evolution of identifiable cancer subclone populations by integration of data generated by steps 4 and 5; This recursive analysis is necessary as individual tissue samples may contain multiple cancer subclone populations with different genome architectures.

7. Establishment of stage and cancer subclone specific cancer genome maps. Cancer genome maps contain multi-layered data of:

7.1. Mutations of genes and regulatory sequences, copy number changes of genes and regulatory sequences, changes of chromosome structure and chromosome number, 7.2. gene expression status, 7.3. putative or ascertained protein function networks (interactomes) and their assumed or demonstrated modifications based on mutation status within the cancer genomes and based on published data, 7.4. assumed mutation probabilities of genes and regulatory elements based on genetic data obtained by step 4, 7.5. putative assignment of mutated or wild type genes or regulatory elements of cancer genomes at specific progression stages in individual patients as: essential genes, non essential fitness modifying genes, fitness neutral genes, tumor suppressor genes/gatekeeper genes, oncogenes, caretaker genes; The assignment process consists of:

7.5.1. assignment of functions of mutated or wild type genes or regulatory elements by their putative functions derived from data obtained by step 7.3., 7.5.2. assignment of functions of mutated or wild type genes or regulatory elements by identification of positive or negative selection of their physical presence in cancer genomes through the process of tumor progression in individual patients based on phylogenetic maps established by step 6. and by considering mutation probabilities determined by step 7.4., 7.5.1 identification of mutations signatures which are indicative of the designation of genes or regulatory elements of cancer genomes at different progression stages; mutation signatures may, inter alia, comprise:

7.5.3.1. Asymmetrical deletions on homologous chromosomes which limit homozygous loss of nearby genes. These genes are likely to represent essential genes or oncogenes (FIG. 2), 7.5.3.2. DNA deletions or loss of function mutations suggesting the presence of tumor suppressor genes, 7.5.3.3. gain of function mutations or translocations, DNA duplications, lack of DNA deletions suggesting the presence of essential genes or oncogenes, 7.5.4. identification of essential genes or oncogenes by considering loss or reduction of physical or functional genome redundancy based on data generated by steps 7.1. and 7.3., 7.6. Recursive modification of 7.3., if necessary, by embedment of data generated through steps 7.1.-7.5.

8. Integration of knowledge generated through steps 6. and 7. in order to explain somatic cancer evolution in individual patients on the basis of genetic instability, external selection forces and the internal effects of the genome architecture on genes and regulatory elements.

9. Identification of putative genes or regulatory elements which may be targeted in order to kill cancer cells or to slow or to stop clinical cancer progression in the patient. Target genes or regulatory elements may be identified by:

9.1. Their designation as essential genes or regulatory elements in cancer cells of the patient but not in normal tissue cells based on knowledge gained by steps 6. to 8.

9.2. Their demonstrable or deducible impact on the process of somatic cancer evolution in the analyzed patient based on the phylogenetic tree of somatic cancer evolution and on the constructed multilayered cancer genome maps. The impact on the process of somatic cancer evolution may be demonstrated by stabilization of the genome architecture despite a high mutation probability or by a permissive effect on further modification of the genome architecture during somatic cancer evolution.

10. In silico and in vitro evaluation of genes or regulatory elements identified by step 9. as potential targets of gene-therapeutic, immunological or pharmaceutical interventions designed to kill cancer cells or to slow or stop cancer progression during individual somatic cancer evolution.

11. Treatment of the patient with the most suitable gene therapy or immunological or pharmaceutical intervention in order to eliminate cancer cells or to slow or stop cancer progression during somatic cancer evolution.

Advantageous Effects of Invention

The described algorithm enables a personalized treatment of cancer patients by targeting genes which do not belong to oncogenes or tumor suppressor genes but have become putative therapeutic targets due to constraints of the tumor cell architecture on individual somatic cancer evolution.

The described algorithm may allow identification of novel anti-cancer drugs, especially when the algorithm is applied on multiple patients with the same cancer entity which allows identification of shared putative target genes or putative regulatory elements for cancer treatment. The described algorithm may allow the use of existing drugs which have been developed to treat other diseases than cancer but which target genes or regulatory elements or metabolic pathways which have become therapeutic targets in a single patient due to constraints of the tumor architecture on individual somatic cancer evolution.

The algorithm may be used for designing software programs which allow the prediction of the natural history of cancer disease in individual patients.

BEST MODE FOR CARRYING OUT THE INVENTION

Best Mode

The best mode of invention is described by the algorithm and by the accompanying FIG. 3.

INDUSTRIAL APPLICABILITY

The described algorithm allows the pharmaceutical industry to identify novel anti-cancer drugs when the algorithm is applied on multiple patients with the same cancer entity which enables identification of shared putative target genes or putative regulatory elements for cancer treatment.

The described algorithm allows health care industry to provide personalized treatment to cancer patients.

The described algorithm allows information technology industry to design and sell software applications which integrate the described algorithm into software programs which allow the prediction of the natural history of cancer disease in individual patients.

What is claimed is:

1. A computer-implemented method for identifying wild type or mutated target genes or regulatory elements for cancer therapy, comprising:
identifying constraints mediated by a cancer genome architecture on somatic cancer evolution in a human cancer patient;
identifying target genes which are involved in mediating the constraints, and which are not from classes of genes including, oncogenes, tumor suppressor genes, or caretaker genes, the identifying the target genes comprising:
constructing a phylogenetic tree of somatic cancer evolution of a malignant human tumor within the human cancer patient based on multiple clinical samples of tissue from the human cancer patient, which are representative of clinical cancer progression within the human cancer patient, wherein the constructing the phylogenetic tree of somatic cancer evolution comprises the steps of:
a) constructing at least one map of clinical cancer progression in individual patients based on the anatomical and temporal occurrence of a primary tumor and its metastases,
b) obtaining DNA, RNA and proteins of unaffected tissue and of samples of the primary tumor, and of regional and distant metastases from the human cancer patient representing clinical cancer progression,
c) extraction of genome wide genetic data out of the obtained tissues in order to determine the cancer genome architecture of analyzed tissue samples by determination of RNA and protein expression, of karyotypes, of gene losses and gains as well as of gene allele losses in tumor tissues; genetic data may be obtained by various molecular methods such as cDNA expression arrays, comparative genomic hybridization arrays, single nucleotide polymorphism arrays, as well as high throughput DNA sequencing,
d) constructing a preliminary phylogenetic tree of the somatic cancer evolution, including clustering of the genetic data obtained by step (c) to obtain information, and,
e) constructing of a definitive phylogenetic tree of somatic cancer evolution further including identifying cancer subclone populations and resolving contradictory results due to mixing of subclones by clustering the genetic data obtained by step (c) and applying the information obtained in step (d);
wherein the cancer genome architecture comprises:

the base composition of genes, of regulatory elements and, if present in cancer cells, of foreign (viral) DNA/RNA sequences, the presence and copy number of wild type or mutated genes, of regulatory elements, and if present in cancer cells, of foreign (viral) DNA/RNA sequences, the physical arrangement of genes, of regulatory elements, and, if present in cancer cells, of foreign (viral) DNA/RNA sequences within chromosomes as well as within mitochondrial DNA, including rearrangements of chromosomes or chromosome fragments, the chromatin organization including epigenetic modifications, interaction of DNA with RNAs and nuclear proteins and nuclear topology of chromosomes, and the status of gene transcription; and, treating the human cancer patient by targeting the identified target genes in order to kill cancer cells, or to slow, or stop clinical cancer progression in the human cancer patient.

2. The method of claim 1, wherein the constructing the phylogenetic tree of somatic cancer evolution causes identification of cancer subclone populations during the somatic cancer evolution.

3. The method of claim 1, wherein the identifying of target genes comprises the identification of the mechanisms of genetic instability within cancer subclone populations within the definitive phylogenetic map of somatic cancer evolution.

4. The method of claim 1, wherein the identifying target genes is performed for at least one of: killing cancer cells, or, 2) slowing or stopping clinical cancer progression in human cancer patients with a specific cancer entity.

5. The method of claim 1, wherein the identifying target genes—comprises: applying at least one of: 1) gene therapy approaches targeting DNA or transcribed RNA, and, 2) pharmacological or immunological approaches targeting translated proteins or pharmacological approaches targeting metabolic pathways of target genes or target regulatory elements are involved.

6. A computer-implemented method for identifying wild type or mutated target genes or regulatory elements for cancer therapy comprising:

identifying constraints mediated by a cancer genome architecture on somatic cancer evolution in a human cancer patient;

identifying target genes which are involved in mediating the constraints, and which are not from classes of genes including, oncogenes, tumor suppressor genes, or caretaker genes, the identifying of the target genes including constructing multilayered cancer genome maps of cancer subclone populations within a definitive phylogenetic tree of somatic cancer evolution;

wherein the multilayered cancer genome maps contain data including:
a) the cancer genome architecture,
b) putative or ascertained protein function networks (interactomes) and their assumed or demonstrated modifications based on mutation status within cancer subclone populations and based on published data,
c) determinations of functional genome redundancy of mutated or wild type genes or regulatory elements of cancer genomes of identified cancer subclone populations; functional genome redundancy of a gene or a regulatory element is defined as the number of additional and different genetic elements coding for the same specific biological function within a cancer genome architecture; functional genome redundancy is lost when only one specific DNA sequence, regardless of its copy number, assumes a specific biological function,
d) assignment of mutated or wild type genes or regulatory elements of cancer genomes of identified cancer subclone populations as: 1) tumor suppressor genes/gatekeeper genes, oncogenes or caretaker genes; and, 2) essential genes, non essential fitness modifying genes or fitness neutral genes; wild type or mutated genes or regulatory elements are designated as essential if their function is essential to sustain survival of the cancer cell within a clinical progression stage or within a cancer cell microenvironment, and,
e) assumed mutation probabilities of genes and regulatory elements based on data on the mechanisms of genetic instability of the cancer subclone populations; and, treating the human cancer patient by targeting the identified target genes in order to kill cancer cells, or to slow, or stop clinical cancer progression in the human cancer patient.

7. The method of claim 6, wherein the assignment of mutated or wild type genes or regulatory elements of cancer genomes of identified cancer subclone populations comprises:
a) assignment of functions of mutated or wild type genes or regulatory elements by their putative functions,
b) assignment of functions of mutated or wild type genes or regulatory elements as essential genes by identification of positive selection of their physical presence in cancer genomes of cancer subclone populations through the process of somatic cancer evolution based on the definitive phylogenetic tree, and by considering mutation probabilities,
c) assignment of functions of mutated or wild type genes or regulatory elements by identification of mutation signatures which are indicative of the designation of at least one of target genes or target regulatory elements of cancer genomes at different progression stages; the mutation signatures include asymmetrical deletions on homologous chromosomes which avoid homozygeous loss of nearby essential genes or oncogenes, DNA deletions or loss of function mutations suggesting the presence of tumor suppressor genes and gain of function mutations, translocations or duplications suggesting oncogenes or essential genes, and,
d) identification of essential genes or oncogenes by identification of loss of functional genome redundancy.

8. The method of claim 7, wherein the at least one of the target genes or the target regulatory elements are identified by their designation as essential genes in cancer subclone population cells of the human cancer patient but not in normal tissue cells.

9. The method of claim 7, wherein the at least one of the target genes or target regulatory elements are additionally identified by their retarding impact on the process of somatic cancer evolution in the analyzed human cancer patient based on the definitive phylogenetic tree of somatic cancer evolution and on the constructed multilayered cancer genome maps; and, treating the human cancer patient by targeting the identified target genes in order to kill cancer cells, or to slow, or stop clinical cancer progression in the human cancer patient.

* * * * *